United States Patent
Shuros

(10) Patent No.: US 12,349,964 B2
(45) Date of Patent: Jul. 8, 2025

(54) PRETREATMENT WAVEFORM FOR IRREVERSIBLE ELECTROPORATION

(71) Applicant: Boston Scientific Scimed Inc., Maple Grove, MN (US)

(72) Inventor: Allan Charles Shuros, St Paul, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 342 days.

(21) Appl. No.: 17/488,217

(22) Filed: Sep. 28, 2021

(65) Prior Publication Data

US 2022/0096151 A1     Mar. 31, 2022

Related U.S. Application Data

(60) Provisional application No. 63/085,452, filed on Sep. 30, 2020.

(51) Int. Cl.
*A61B 18/12* (2006.01)
*A61B 18/14* (2006.01)
*A61B 18/00* (2006.01)

(52) U.S. Cl.
CPC ...... *A61B 18/1492* (2013.01); *A61B 18/1206* (2013.01); *A61B 2018/00577* (2013.01);
(Continued)

(58) Field of Classification Search
CPC ...... A61B 2018/00613; A61B 18/1492; A61B 18/1206; A61B 2018/00577; A61B 2018/126

See application file for complete search history.

(56) References Cited

U.S. PATENT DOCUMENTS

| 4,200,104 A | 4/1980 | Harris |
| 4,470,407 A | 9/1984 | Hussein |

(Continued)

FOREIGN PATENT DOCUMENTS

| EP | 1042990 A1 | 10/2000 |
| EP | 1125549 A2 | 8/2001 |

(Continued)

OTHER PUBLICATIONS

International Search Report and Written Opinion received for PCT Patent Application No. PCT/US2021/052478, mailed on Mar. 30, 2022, 13 pages.

(Continued)

*Primary Examiner* — Jaymi E Della
(74) *Attorney, Agent, or Firm* — Nelson Mullins Riley & Scarborough LLP

(57) ABSTRACT

An electroporation ablation system for treating targeted tissue in a patient. The electroporation ablation system including an ablation catheter and an electroporation generator. The ablation catheter including a handle, a shaft having a distal end, and catheter electrodes situated at the distal end of the shaft and spatially arranged to generate electric fields in the targeted tissue in response to electrical pulses. The electroporation generator operatively coupled to the catheter electrodes and configured to deliver the electrical pulses in an irreversible electroporation pulse sequence that includes a preconditioning pulse sequence and an electroporation pulse sequence to one or more catheter electrodes. Wherein the preconditioning pulse sequence includes preconditioning electrical pulses configured to cause electrolysis near the targeted tissue and tetanizing skeletal muscle stimulation in the patient.

19 Claims, 5 Drawing Sheets

(52) U.S. Cl.
CPC ............... *A61B 2018/00613* (2013.01); *A61B 2018/1253* (2013.01); *A61B 2018/126* (2013.01); *A61B 2562/0219* (2013.01)

(56) References Cited

U.S. PATENT DOCUMENTS

| | | | |
|---|---|---|---|
| 4,739,759 A | 4/1988 | Rexroth et al. | |
| 5,234,004 A | 8/1993 | Hascoet et al. | |
| 5,242,441 A | 9/1993 | Avitall | |
| 5,257,635 A | 11/1993 | Langberg | |
| 5,281,213 A | 1/1994 | Milder et al. | |
| 5,304,214 A | 4/1994 | Deford et al. | |
| 5,306,296 A | 4/1994 | Wright et al. | |
| 5,334,193 A | 8/1994 | Nardella | |
| 5,341,807 A | 8/1994 | Nardella | |
| 5,342,301 A | 8/1994 | Saab | |
| 5,398,683 A | 3/1995 | Edwards et al. | |
| 5,443,463 A | 8/1995 | Stern et al. | |
| 5,454,370 A | 10/1995 | Avitall | |
| 5,515,848 A | 5/1996 | Corbett et al. | |
| 5,531,685 A | 7/1996 | Hemmer et al. | |
| 5,545,161 A | 8/1996 | Imran | |
| 5,558,091 A | 9/1996 | Acker et al. | |
| 5,578,040 A | 11/1996 | Smith | |
| 5,617,854 A | 4/1997 | Munsif | |
| 5,624,430 A | 4/1997 | Eton et al. | |
| 5,662,108 A | 9/1997 | Budd et al. | |
| 5,667,491 A | 9/1997 | Pliquett et al. | |
| 5,672,170 A | 9/1997 | Cho et al. | |
| 5,700,243 A | 12/1997 | Narciso, Jr. | |
| 5,702,438 A | 12/1997 | Avitall | |
| 5,706,823 A | 1/1998 | Wodlinger | |
| 5,722,400 A | 3/1998 | Ockuly et al. | |
| 5,722,402 A | 3/1998 | Swanson et al. | |
| 5,749,914 A | 5/1998 | Janssen | |
| 5,779,699 A | 7/1998 | Lipson | |
| 5,788,692 A | 8/1998 | Campbell et al. | |
| 5,810,762 A | 9/1998 | Hofmann | |
| 5,833,710 A | 11/1998 | Jacobson | |
| 5,836,874 A | 11/1998 | Swanson et al. | |
| 5,836,942 A | 11/1998 | Netherly et al. | |
| 5,836,947 A | 11/1998 | Fleischman et al. | |
| 5,843,154 A | 12/1998 | Osypka | |
| 5,849,028 A | 12/1998 | Chen | |
| 5,863,291 A | 1/1999 | Schaer | |
| 5,868,736 A | 2/1999 | Swanson et al. | |
| 5,871,523 A | 2/1999 | Fleischman et al. | |
| 5,876,336 A | 3/1999 | Swanson et al. | |
| 5,885,278 A | 3/1999 | Fleischman | |
| 5,895,404 A | 4/1999 | Ruiz | |
| 5,899,917 A | 5/1999 | Edwards et al. | |
| 5,904,709 A | 5/1999 | Arndt et al. | |
| 5,916,158 A | 6/1999 | Webster, Jr. | |
| 5,916,213 A | 6/1999 | Haissaguerre et al. | |
| 5,921,924 A | 7/1999 | Avitall | |
| 5,928,269 A | 7/1999 | Alt | |
| 5,928,270 A | 7/1999 | Ramsey, III | |
| 6,002,955 A | 12/1999 | Willems et al. | |
| 6,006,131 A | 12/1999 | Cooper et al. | |
| 6,009,351 A | 12/1999 | Flachman | |
| 6,014,579 A | 1/2000 | Pomeranz et al. | |
| 6,029,671 A | 2/2000 | Stevens et al. | |
| 6,033,403 A | 3/2000 | Tu et al. | |
| 6,035,238 A | 3/2000 | Ingle et al. | |
| 6,045,550 A | 4/2000 | Simpson et al. | |
| 6,059,779 A | 5/2000 | Mills | |
| 6,068,653 A | 5/2000 | LaFontaine | |
| 6,071,274 A | 6/2000 | Thompson et al. | |
| 6,071,281 A | 6/2000 | Burnside et al. | |
| 6,074,389 A | 6/2000 | Levine et al. | |
| 6,076,012 A | 6/2000 | Swanson et al. | |
| 6,090,104 A | 7/2000 | Webster, Jr. | |
| 6,096,036 A | 8/2000 | Bowe et al. | |
| 6,113,595 A | 9/2000 | Muntermann | |
| 6,119,041 A | 9/2000 | Pomeranz et al. | |
| 6,120,500 A | 9/2000 | Bednarek et al. | |
| 6,146,381 A | 11/2000 | Bowe et al. | |
| 6,164,283 A | 12/2000 | Lesh | |
| 6,167,291 A | 12/2000 | Barajas et al. | |
| 6,171,305 B1 | 1/2001 | Sherman | |
| 6,216,034 B1 | 4/2001 | Hofmann et al. | |
| 6,219,582 B1 | 4/2001 | Hofstad et al. | |
| 6,223,085 B1 | 4/2001 | Dann et al. | |
| 6,231,518 B1 | 5/2001 | Grabek et al. | |
| 6,245,064 B1 | 6/2001 | Lesh et al. | |
| 6,251,107 B1 | 6/2001 | Schaer | |
| 6,251,128 B1 | 6/2001 | Knopp et al. | |
| 6,270,476 B1 | 8/2001 | Santoianni et al. | |
| 6,272,384 B1 | 8/2001 | Simon et al. | |
| 6,287,306 B1 | 9/2001 | Kroll et al. | |
| 6,314,963 B1 | 11/2001 | Vaska et al. | |
| 6,322,559 B1 | 11/2001 | Daulton et al. | |
| 6,350,263 B1 | 2/2002 | Wetzig et al. | |
| 6,370,412 B1 | 4/2002 | Armoundas et al. | |
| 6,391,024 B1 | 5/2002 | Sun et al. | |
| 6,447,505 B2 | 9/2002 | McGovern et al. | |
| 6,464,699 B1 | 10/2002 | Swanson | |
| 6,470,211 B1 | 10/2002 | Ideker et al. | |
| 6,502,576 B1 | 1/2003 | Lesh | |
| 6,503,247 B2 | 1/2003 | Swartz et al. | |
| 6,517,534 B1 | 2/2003 | McGovern et al. | |
| 6,527,724 B1 | 3/2003 | Fenici | |
| 6,527,767 B2 | 3/2003 | Wang et al. | |
| 6,592,581 B2 | 7/2003 | Bowe | |
| 6,595,991 B2 | 7/2003 | Toellner et al. | |
| 6,607,520 B2 | 8/2003 | Keane | |
| 6,623,480 B1 | 9/2003 | Kuo et al. | |
| 6,638,278 B2 | 10/2003 | Falwell et al. | |
| 6,666,863 B2 | 12/2003 | Wentzel et al. | |
| 6,669,693 B2 | 12/2003 | Friedman | |
| 6,702,811 B2 | 3/2004 | Stewart et al. | |
| 6,719,756 B1 | 4/2004 | Muntermann | |
| 6,723,092 B2 | 4/2004 | Brown et al. | |
| 6,728,563 B2 | 4/2004 | Rashidi | |
| 6,743,225 B2 | 6/2004 | Sanchez et al. | |
| 6,743,226 B2 | 6/2004 | Cosman et al. | |
| 6,743,239 B1 | 6/2004 | Kuehn et al. | |
| 6,764,486 B2 | 7/2004 | Natale | |
| 6,780,181 B2 | 8/2004 | Kroll et al. | |
| 6,805,128 B1 | 10/2004 | Pless et al. | |
| 6,807,447 B2 | 10/2004 | Griffin, III | |
| 6,892,091 B1 | 5/2005 | Ben-Haim et al. | |
| 6,893,438 B2 | 5/2005 | Hall et al. | |
| 6,926,714 B1 | 8/2005 | Sra | |
| 6,955,173 B2 | 10/2005 | Lesh | |
| 6,960,206 B2 | 11/2005 | Keane | |
| 6,960,207 B2 | 11/2005 | Vanney et al. | |
| 6,972,016 B2 | 12/2005 | Hill et al. | |
| 6,973,339 B2 | 12/2005 | Govari | |
| 6,979,331 B2 | 12/2005 | Hintringer et al. | |
| 6,984,232 B2 | 1/2006 | Vanney et al. | |
| 6,985,776 B2 | 1/2006 | Kane et al. | |
| 7,001,383 B2 | 2/2006 | Keidar | |
| 7,041,095 B2 | 5/2006 | Wang et al. | |
| 7,113,831 B2 | 9/2006 | Hooven | |
| 7,171,263 B2 | 1/2007 | Darvish et al. | |
| 7,182,725 B2 | 2/2007 | Bonan et al. | |
| 7,195,628 B2 | 3/2007 | Falkenberg | |
| 7,207,988 B2 | 4/2007 | Leckrone et al. | |
| 7,207,989 B2 | 4/2007 | Pike et al. | |
| 7,229,402 B2 | 6/2007 | Diaz et al. | |
| 7,229,437 B2 | 6/2007 | Johnson et al. | |
| 7,250,049 B2 | 7/2007 | Roop et al. | |
| 7,282,057 B2 | 10/2007 | Surti et al. | |
| 7,285,116 B2 | 10/2007 | De et al. | |
| 7,285,119 B2 | 10/2007 | Stewart et al. | |
| 7,326,208 B2 | 2/2008 | Vanney et al. | |
| 7,346,379 B2 | 3/2008 | Eng et al. | |
| 7,367,974 B2 | 5/2008 | Haemmerich et al. | |
| 7,374,567 B2 | 5/2008 | Heuser | |
| 7,387,629 B2 | 6/2008 | Vanney et al. | |
| 7,387,630 B2 | 6/2008 | Mest | |
| 7,387,636 B2 | 6/2008 | Cohn et al. | |
| 7,416,552 B2 | 8/2008 | Paul et al. | |

(56) References Cited

U.S. PATENT DOCUMENTS

| | | |
|---|---|---|
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,643,876 B2 | 1/2010 | Zhang et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro'et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harlev et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | Mcgee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emmons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,117,707 B2 | 11/2018 | Garcia et al. |
| 10,130,423 B1 | 11/2018 | Viswanathan et al. |
| 10,172,673 B2 | 1/2019 | Viswanathan et al. |
| 10,292,755 B2 | 5/2019 | Arena et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,448,989 B2 | 10/2019 | Arena et al. |
| 10,507,302 B2 | 12/2019 | Leeflang et al. |

(56) References Cited

U.S. PATENT DOCUMENTS

| | | |
|---|---|---|
| 10,512,505 B2 | 12/2019 | Viswanathan |
| 10,512,779 B2 | 12/2019 | Viswanathan et al. |
| 10,517,672 B2 | 12/2019 | Long |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Prestel |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek-Petric |
| 2003/0229379 A1 | 12/2003 | Maynard |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0236419 A1 | 11/2004 | Milo |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2005/0288730 A1 | 12/2005 | Deem et al. |
| 2006/0009755 A1 | 1/2006 | Sra |
| 2006/0009759 A1 | 1/2006 | Christian et al. |
| 2006/0015095 A1 | 1/2006 | Desinger et al. |
| 2006/0015165 A1 | 1/2006 | Bertolero et al. |
| 2006/0024359 A1* | 2/2006 | Walker .............. A61K 9/0009 604/20 |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Sliwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0249518 A1 | 10/2008 | Warnking et al. |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2008/0319436 A1 | 12/2008 | Daniel et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076409 A1 | 3/2009 | Wu et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0198300 A1 | 8/2009 | Zhang et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0204619 A1 | 8/2010 | Rosenberg |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1 | 2/2011 | Hopenfeld |
| 2011/0098694 A1 | 4/2011 | Long |
| 2011/0106221 A1 | 5/2011 | Neal et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De et al. |
| 2012/0029512 A1 | 2/2012 | Willard et al. |
| 2012/0046570 A1 | 2/2012 | Mllegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078320 A1 | 3/2012 | Schotzko et al. |
| 2012/0078343 A1 | 3/2012 | Fish |
| 2012/0089089 A1 | 4/2012 | Swain et al. |
| 2012/0095459 A1 | 4/2012 | Callas et al. |

(56) References Cited

U.S. PATENT DOCUMENTS

| | | |
|---|---|---|
| 2012/0095461 A1 | 4/2012 | Herscher et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1 | 6/2013 | Ding et al. |
| 2013/0172715 A1 | 7/2013 | Just et al. |
| 2013/0172864 A1 | 7/2013 | Ibrahim et al. |
| 2013/0172875 A1 | 7/2013 | Govari et al. |
| 2013/0184702 A1 | 7/2013 | Neal et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Hue-Teh |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0253140 A1 | 9/2014 | Gilbert |
| 2014/0276712 A1 | 9/2014 | Mallin et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0327944 A1 | 11/2015 | Neal et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0183877 A1 | 6/2016 | Williams et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0296269 A1* | 10/2016 | Rubinsky ............... A61N 1/327 |
| 2016/0310211 A1 | 10/2016 | Long |
| 2016/0324564 A1 | 11/2016 | Gerlach et al. |
| 2016/0324573 A1 | 11/2016 | Mickelson et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |

(56) References Cited

U.S. PATENT DOCUMENTS

| | | |
|---|---|---|
| 2017/0035499 A1* | 2/2017 | Stewart ................ A61N 1/327 |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0120048 A1 | 5/2017 | He et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Mswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0133460 A1 | 5/2018 | Townley et al. |
| 2018/0168511 A1 | 6/2018 | Hall et al. |
| 2018/0184982 A1 | 7/2018 | Basu et al. |
| 2018/0193082 A1* | 7/2018 | Rubinsky ............ A61B 18/1402 |
| 2018/0193090 A1 | 7/2018 | De et al. |
| 2018/0200497 A1 | 7/2018 | Mickelsen |
| 2018/0289417 A1 | 10/2018 | Schweitzer et al. |
| 2018/0303488 A1 | 10/2018 | Hill |
| 2018/0311497 A1 | 11/2018 | Viswanathan et al. |
| 2018/0344393 A1 | 12/2018 | Gruba et al. |
| 2018/0360534 A1 | 12/2018 | Teplitsky et al. |
| 2019/0038171 A1 | 2/2019 | Howard |
| 2019/0046791 A1 | 2/2019 | Ebbers et al. |
| 2019/0069950 A1 | 3/2019 | Viswanathan et al. |
| 2019/0125439 A1 | 5/2019 | Rohl et al. |
| 2019/0151015 A1 | 5/2019 | Viswanathan et al. |
| 2019/0183378 A1 | 6/2019 | Mosesov et al. |
| 2019/0209238 A1 | 7/2019 | Jimenez |
| 2019/0223938 A1 | 7/2019 | Arena et al. |
| 2019/0223950 A1 | 7/2019 | Gelbart et al. |
| 2019/0231421 A1 | 8/2019 | Viswanathan et al. |
| 2019/0233809 A1 | 8/2019 | Neal et al. |
| 2019/0256839 A1 | 8/2019 | Neal et al. |
| 2019/0269912 A1 | 9/2019 | Viswanathan et al. |
| 2019/0328445 A1 | 10/2019 | Sano et al. |
| 2019/0336198 A1 | 11/2019 | Viswanathan et al. |
| 2019/0336207 A1 | 11/2019 | Viswanathan |
| 2019/0336757 A1 | 11/2019 | Rodriguez et al. |
| 2019/0376055 A1 | 12/2019 | Davalos et al. |
| 2020/0107879 A1 | 4/2020 | Stewart et al. |
| 2021/0031020 A1 | 2/2021 | Mickelsen |
| 2022/0000548 A1 | 1/2022 | Mickelsen |

FOREIGN PATENT DOCUMENTS

| | | | |
|---|---|---|---|
| EP | 0797956 | B1 | 6/2003 |
| EP | 1340469 | A1 | 9/2003 |
| EP | 1127552 | B1 | 6/2006 |
| EP | 1803411 | A2 | 7/2007 |
| EP | 1009303 | B1 | 6/2009 |
| EP | 2213729 | A2 | 8/2010 |
| EP | 2382935 | A1 | 11/2011 |
| EP | 2425871 | A2 | 3/2012 |
| EP | 2532320 | A2 | 12/2012 |
| EP | 2587275 | A1 | 5/2013 |
| EP | 2663227 | A1 | 11/2013 |
| EP | 1909678 | B1 | 1/2014 |
| EP | 2217165 | B1 | 3/2014 |
| EP | 2376193 | B1 | 3/2014 |
| EP | 2708181 | A1 | 3/2014 |
| EP | 2777579 | A1 | 9/2014 |
| EP | 2777585 | A1 | 9/2014 |
| EP | 2934307 | A1 | 10/2015 |
| EP | 3056242 | A1 | 8/2016 |
| EP | 3111871 | A1 | 1/2017 |
| EP | 3151773 | B1 | 4/2018 |
| JP | 06-507797 | A | 9/1994 |
| JP | 10-510745 | A | 10/1998 |
| JP | 2000-508196 | A | 7/2000 |
| JP | 2005-003394 | A | 1/2005 |
| JP | 2005-516666 | A | 6/2005 |
| JP | 2006-506184 | A | 2/2006 |
| JP | 2007-325935 | A | 12/2007 |
| JP | 2008-538997 | A | 11/2008 |
| JP | 2009-500129 | A | 1/2009 |
| JP | 2011-509158 | A | 3/2011 |
| JP | 2012-050538 | A | 3/2012 |
| JP | 2016-515869 | A | 6/2016 |
| JP | 2019-503773 | A | 2/2019 |
| JP | 2019-522515 | A | 8/2019 |
| WO | 92/07622 | A1 | 5/1992 |
| WO | 92/21278 | A1 | 12/1992 |
| WO | 92/21285 | A1 | 12/1992 |
| WO | 94/07413 | A1 | 4/1994 |
| WO | 97/24073 | A1 | 7/1997 |
| WO | 97/25917 | A1 | 7/1997 |
| WO | 97/37719 | A1 | 10/1997 |
| WO | 99/04851 | A1 | 2/1999 |
| WO | 99/22659 | A1 | 5/1999 |
| WO | 99/56650 | A1 | 11/1999 |
| WO | 99/59486 | A2 | 11/1999 |
| WO | 02/56782 | A2 | 7/2002 |
| WO | 03/53289 | A1 | 7/2003 |
| WO | 03/65916 | A1 | 8/2003 |
| WO | 2004/045442 | A1 | 6/2004 |
| WO | 2004/086994 | A1 | 10/2004 |
| WO | 2005/046487 | A1 | 5/2005 |
| WO | 2006/115902 | A2 | 11/2006 |
| WO | 2007/006055 | A2 | 1/2007 |
| WO | 2007/079438 | A2 | 7/2007 |
| WO | 2009/082710 | A1 | 7/2009 |
| WO | 2009/089343 | A1 | 7/2009 |
| WO | 2009/137800 | A2 | 11/2009 |
| WO | 2010/014480 | A1 | 2/2010 |
| WO | 2011/028310 | A1 | 3/2011 |
| WO | 2011/154805 | A1 | 12/2011 |
| WO | 2012/051433 | A2 | 4/2012 |
| WO | 2012/097067 | A1 | 7/2012 |
| WO | 2012/153928 | A2 | 11/2012 |
| WO | 2012/156944 | A1 | 11/2012 |
| WO | 2013/019385 | A1 | 2/2013 |
| WO | 2014/025394 | A1 | 2/2014 |
| WO | 2014/031800 | A1 | 2/2014 |
| WO | 2014/036439 | A2 | 3/2014 |
| WO | 2014/100579 | A1 | 6/2014 |
| WO | 2014/160832 | A2 | 10/2014 |
| WO | 2015/066322 | A1 | 5/2015 |
| WO | 2015/099786 | A1 | 7/2015 |
| WO | 2015/103530 | A1 | 7/2015 |
| WO | 2015/103574 | A1 | 7/2015 |
| WO | 2015/130824 | A1 | 9/2015 |
| WO | 2015/140741 | A1 | 9/2015 |
| WO | 2015/143327 | A1 | 9/2015 |
| WO | 2015/171921 | A2 | 11/2015 |
| WO | 2015/175944 | A1 | 11/2015 |
| WO | 2015/192018 | A1 | 12/2015 |
| WO | 2015/192027 | A1 | 12/2015 |
| WO | 2016/059027 | A1 | 4/2016 |
| WO | 2016/060983 | A1 | 4/2016 |
| WO | 2016/081650 | A1 | 5/2016 |
| WO | 2016/090175 | A1 | 6/2016 |
| WO | 2017/093926 | A1 | 6/2017 |
| WO | 2017/119934 | A1 | 7/2017 |
| WO | 2017/120169 | A1 | 7/2017 |

(56) References Cited

FOREIGN PATENT DOCUMENTS

| WO | 2017/192477 A1 | 11/2017 | |
| WO | 2017/192495 A1 | 11/2017 | |
| WO | 2017/218734 A1 | 12/2017 | |
| WO | 2018/005511 A1 | 1/2018 | |
| WO | 2018/191149 A1 | 10/2018 | |
| WO | 2018/200800 A1 | 11/2018 | |
| WO | 2019/118436 A1 | 6/2019 | |
| WO | 2019/133606 A1 | 7/2019 | |
| WO | 2019/234133 A1 | 12/2019 | |
| WO | WO-2020051241 A1 * | 3/2020 | ......... A61B 18/1206 |

OTHER PUBLICATIONS

Du Pre, B.C. et al., "Minimal coronary artery damage by myocardial electroporation ablation," Europace, 15(1):144-149 (2013).

Hobbs, E. P., "Investor Relations Update: Tissue Ablation via Irreversible Electroporation (IRE)," Powerpoint (2004), 16 pages.

Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].

Madhavan, M. et al., "Novel Percutaneous Epicardial Autonomic Modulation in the Canine for Atrial Fibrillation: Results of an Efficacy and Safety Study," Pace, 00:1-11 (2016).

Neven, K. et al., "Epicardial linear electroporation ablation and lesion size," Heart Rhythm, 11:1465-1470 (2014).

Neven, K. et al., "Myocardial Lesion Size After Epicardial Electroporation Catheter Ablation After Subxiphoid Puncture," Circ Arrhythm Electrophysiol., 7(4):728-733 (2014).

Neven, K. et al., "Safety and Feasibility of Closed Chest Epicardial Catheter Ablation Using Electroporation," Circ Arrhythm Electrophysiol., 7:913-919 (2014).

Van Driel, V.J.H.M. et al., "Low vulnerability of the right phrenic nerve to electroporation ablation," Heart Rhythm, 12:1838-1844 (2015).

Van Driel, V.J.H.M. et al., "Pulmonary Vein Stenosis After Catheter Ablation Electroporation Versus Radiofrequency," Circ Arrhythm Electrophysiol., 7(4):734-738 (2014).

Wittkampf, F.H. et al., "Feasibility of Electroporation for the Creation of Pulmonary Vein Ostial Lesions," J Cardiovasc Electrophysiol, 22(3):302-309 (Mar. 2011).

Wittkampf, F.H. et al., "Myocardial Lesion Depth With Circular Electroporation Ablation," Circ. Arrhythm Electrophysiol., 5(3):581-586 (2012).

* cited by examiner

PRETREATMENT WAVEFORM FOR IRREVERSIBLE ELECTROPORATION

CROSS REFERENCE TO RELATED APPLICATION

This application claims priority to Provisional Application No. 63/085,452, filed Sep. 30, 2020, which is herein incorporated by reference in its entirety.

TECHNICAL FIELD

The present disclosure relates to medical apparatus, systems, and methods for ablating tissue in a patient. More specifically, the present disclosure relates to medical apparatus, systems, and methods for ablation of tissue by electroporation.

BACKGROUND

Ablation procedures are used to treat many different conditions in patients. Ablation may be used to treat cardiac arrhythmias, benign tumors, cancerous tumors, and to control bleeding during surgery. Usually, ablation is accomplished through thermal ablation techniques including radio-frequency (RF) ablation and cryoablation. In RF ablation, a probe is inserted into the patient and radio frequency waves are transmitted through the probe to the surrounding tissue. The radio frequency waves generate heat, which destroys surrounding tissue and cauterizes blood vessels. In cryoablation, a hollow needle or cryoprobe is inserted into the patient and cold, thermally conductive fluid is circulated through the probe to freeze and kill the surrounding tissue. RF ablation and cryoablation techniques indiscriminately kill tissue through cell necrosis, which may damage or kill otherwise healthy tissue, such as tissue in the esophagus, phrenic nerve cells, and tissue in the coronary arteries.

Another ablation technique uses electroporation. In electroporation, or electro-permeabilization, an electric field is applied to cells to increase the permeability of the cell membrane. The electroporation may be reversible or irreversible, depending on the strength of the electric field. If the electroporation is reversible, the increased permeability of the cell membrane may be used to introduce chemicals, drugs, and/or deoxyribonucleic acid (DNA) into the cell, prior to the cell healing and recovering. If the electroporation is irreversible, the affected cells are killed through apoptosis.

Irreversible electroporation (IRE) may be used as a non-thermal ablation technique. In IRE, trains of short, high voltage pulses are used to generate electric fields that are strong enough to kill cells through apoptosis. In ablation of cardiac tissue, IRE may be a safe and effective alternative to the indiscriminate killing of thermal ablation techniques, such as RF ablation and cryoablation. IRE may be used to kill targeted tissue, such as myocardium tissue, by using an electric field strength and duration that kills the targeted tissue but does not permanently damage other cells or tissue, such as non-targeted myocardium tissue, red blood cells, vascular smooth muscle tissue, endothelium tissue, and nerve cells.

In some IRE procedures, the electroporation electrical pulses cause the unwanted side effect of skeletal muscle stimulation (SMS) and engagement. One way to reduce SMS, is to refine the IRE electrical pulses, such that the pulses are optimized to avoid SMS. Often this results in having a smaller ablation electric field and in creating smaller lesions. A way of delivering effective IRE energies while avoiding SMS is needed.

SUMMARY

In Example 1, an electroporation ablation system for treating targeted tissue in a patient. The electroporation ablation system including an ablation catheter and an electroporation generator. The ablation catheter including a handle, a shaft having a distal end, and catheter electrodes situated at the distal end of the shaft and spatially arranged to generate electric fields in the targeted tissue in response to electrical pulses. The electroporation generator operatively coupled to the catheter electrodes and configured to deliver the electrical pulses in an irreversible electroporation pulse sequence that includes a preconditioning pulse sequence and an electroporation pulse sequence to one or more catheter electrodes. Wherein the preconditioning pulse sequence includes preconditioning electrical pulses configured to cause electrolysis near the targeted tissue and tetanizing skeletal muscle stimulation in the patient.

In Example 2, the electroporation ablation system of Example 1, comprising a surface patch electrode attached to the patient and configured to generate electric fields in the patient in response to the electrical pulses.

In Example 3, the electroporation ablation system of Example 2, wherein the preconditioning pulse sequence includes unipolar electrical pulses that are sourced from the surface patch electrode and sunk through the one or more catheter electrodes.

In Example 4, the electroporation ablation system of Example 2, wherein the preconditioning pulse sequence includes unipolar electrical pulses that are sourced from the one or more catheter electrodes and sunk through the surface patch electrode.

In Example 5, the electroporation ablation system of any of Examples 1-4, wherein the preconditioning pulse sequence includes bipolar electrical pulses that are sourced from at least one of the one or more catheter electrodes and sunk through at least another one of the one or more catheter electrodes.

In Example 6, the electroporation ablation system of any of Examples 1-5, wherein the preconditioning pulse sequence includes preconditioning pulses delivered at a selected frequency.

In Example 7, the electroporation ablation system of any of Examples 1-6, wherein the preconditioning pulse sequence includes preconditioning pulses ramped up in voltage from a lower voltage to a higher voltage over time.

In Example 8, the electroporation ablation system of any of Examples 1-7, wherein the preconditioning pulse sequence includes preconditioning pulses that include an exponentially decaying backside waveform that causes electrolysis near the targeted tissue.

In Example 9, the electroporation ablation system of any of Examples 1-8, wherein the preconditioning pulse sequence includes preconditioning pulses that are monophasic.

In Example 10, the electroporation ablation system of any of Examples 1-9, wherein the irreversible electroporation pulse sequence, including the preconditioning pulse sequence and the electroporation pulse sequence, is delivered to the patient in one or more of a refractory time of a heart of the patient, less than 330 milliseconds, and in a 100-250 millisecond window.

In Example 11, the electroporation ablation system of any of Examples 1-10, wherein the electroporation pulse sequence is delivered within the preconditioning pulse sequence.

In Example 12, the electroporation ablation system of any of Examples 1-11, wherein the electroporation pulse sequence includes bipolar electrical pulses delivered to one or more catheter electrode pairs of the catheter electrodes.

In Example 13, the electroporation ablation system of any of Examples 1-12, comprising an accelerometer configured to monitor skeletal muscle stimulation of the patient and wherein the electroporation ablation system is a closed loop system such that the electroporation generator is configured to deliver the preconditioning pulse sequence, detect tetany in the patient, and then deliver the electroporation pulse sequence, and wherein local impedance is measured to calculate pre-ablation and post-ablation values to evaluate lesion efficacy.

In Example 14, an electroporation ablation system for treating targeted tissue in a patient. The electroporation ablation system including an ablation catheter and an electroporation generator. The ablation catheter including a handle, a shaft having a distal end, and catheter electrodes situated at the distal end of the shaft and spatially arranged to generate electric fields in the targeted tissue in response to electrical pulses. The electroporation generator operatively coupled to multiple electrodes including one or more of a surface patch electrode and one or more catheter electrodes and configured to deliver the electrical pulses in an irreversible electroporation pulse sequence that includes a preconditioning pulse sequence and an electroporation pulse sequence to the multiple electrodes, wherein the electroporation generator delivers the electroporation pulse sequence during the preconditioning pulse sequence.

In Example 15, the electroporation ablation system of Example 14, wherein the preconditioning pulse sequence includes electrical pulses configured to cause electrolysis near the targeted tissue and tetanizing skeletal muscle stimulation in the patient.

In Example 16, an electroporation ablation system for treating targeted tissue in a patient. The electroporation ablation system including an ablation catheter and an electroporation generator. The ablation catheter including a handle, a shaft having a distal end, and catheter electrodes situated at the distal end of the shaft and spatially arranged to generate electric fields in the targeted tissue in response to electrical pulses. The electroporation generator operatively coupled to the catheter electrodes and configured to deliver the electrical pulses in an irreversible electroporation pulse sequence that includes a preconditioning pulse sequence and an electroporation pulse sequence to one or more catheter electrodes, wherein the preconditioning pulse sequence includes preconditioning electrical pulses configured to cause electrolysis near the targeted tissue and tetanizing skeletal muscle stimulation in the patient.

In Example 17, the electroporation ablation system of Example 16, comprising a surface patch electrode attached to the patient and configured to generate electric fields in the patient in response to the electrical pulses.

In Example 18, the electroporation ablation system of Example 16, wherein the preconditioning pulse sequence includes unipolar electrical pulses that are sourced from the surface patch electrode and sunk through the one or more catheter electrodes.

In Example 19, the electroporation ablation system of Example 16, wherein the preconditioning pulse sequence includes unipolar electrical pulses that are sourced from the one or more catheter electrodes and sunk through the surface patch electrode.

In Example 20, the electroporation ablation system of Example 16, wherein the preconditioning pulse sequence includes bipolar electrical pulses that are sourced from at least one of the one or more catheter electrodes and sunk through at least another one of the one or more catheter electrodes.

In Example 21, the electroporation ablation system of Example 16, wherein the preconditioning pulse sequence includes preconditioning pulses delivered at a selected frequency.

In Example 22, the electroporation ablation system of Example 16, wherein the preconditioning pulse sequence includes preconditioning pulses ramped up in voltage from a lower voltage to a higher voltage over time.

In Example 23, the electroporation ablation system of Example 16, wherein the preconditioning pulse sequence includes preconditioning pulses that include an exponentially decaying backside waveform that causes electrolysis near the targeted tissue.

In Example 24, the electroporation ablation system of Example 16, wherein the preconditioning pulse sequence includes preconditioning pulses that are monophasic.

In Example 25, the electroporation ablation system of Example 16, wherein the irreversible electroporation pulse sequence, including the preconditioning pulse sequence and the electroporation pulse sequence, is delivered to the patient in one or more of a refractory time of a heart of the patient, less than 330 milliseconds, and in a 100-250 millisecond window.

In Example 26, the electroporation ablation system of Example 16, wherein the electroporation pulse sequence is delivered within the preconditioning pulse sequence.

In Example 27, the electroporation ablation system of Example 16, wherein the electroporation pulse sequence includes bipolar electrical pulses delivered to one or more catheter electrode pairs of the catheter electrodes.

In Example 28, the electroporation ablation system of Example 16, comprising an accelerometer configured to monitor skeletal muscle stimulation of the patient and wherein the electroporation ablation system is a closed loop system such that the electroporation generator is configured to deliver the preconditioning pulse sequence, detect tetany in the patient, and then deliver the electroporation pulse sequence, and wherein local impedance is measured to calculate pre-ablation and post-ablation values to evaluate lesion efficacy.

In Example 29, an electroporation ablation system for treating targeted tissue in a patient. The electroporation ablation system including an ablation catheter and an electroporation generator. The ablation catheter including a handle, a shaft having a distal end, and catheter electrodes situated at the distal end of the shaft and spatially arranged to generate electric fields in the targeted tissue in response to electrical pulses. The electroporation generator operatively coupled to multiple electrodes including one or more of a surface patch electrode and one or more catheter electrodes and configured to deliver the electrical pulses in an irreversible electroporation pulse sequence that includes a preconditioning pulse sequence and an electroporation pulse sequence to the multiple electrodes, wherein the electroporation generator delivers the electroporation pulse sequence during the preconditioning pulse sequence.

In Example 30, the electroporation ablation system of Example 29, wherein the preconditioning pulse sequence includes preconditioning electrical pulses configured to cause electrolysis near the targeted tissue and tetanizing skeletal muscle stimulation in the patient.

In Example 31, the electroporation ablation system of Example 29, wherein the electroporation pulse sequence includes bipolar electrical pulses delivered to selected pairs of the catheter electrodes.

In Example 32, a method of ablating targeted tissue in a patient by irreversible electroporation. The method comprising delivering an irreversible electroporation pulse sequence including delivering a preconditioning pulse sequence between multiple electrodes including one or more of a surface patch electrode and one or more catheter electrodes on a catheter to cause electrolysis near the targeted tissue and tetanizing skeletal muscle stimulation in the patient, and delivering an electroporation pulse sequence to the multiple electrodes to cause irreversible electroporation ablation of the targeted tissue.

In Example 33, the method of Example 32, wherein delivering a preconditioning pulse sequence includes delivering electrical pulses that ramp up in voltage from a lower voltage to a higher voltage over time and wherein one or more of the electrical pulses include an exponentially decaying backside waveform.

In Example 34, the method of Example 32, wherein the electroporation pulse sequence is delivered during the preconditioning pulse sequence.

In Example 35, the method of Example 32, comprising monitoring an accelerometer on the patient and in a closed loop system, delivering the preconditioning pulse sequence to achieve tetany in the patient, detecting tetany in the patient via the accelerometer, and delivering the electroporation pulse sequence after tetany has been achieved.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
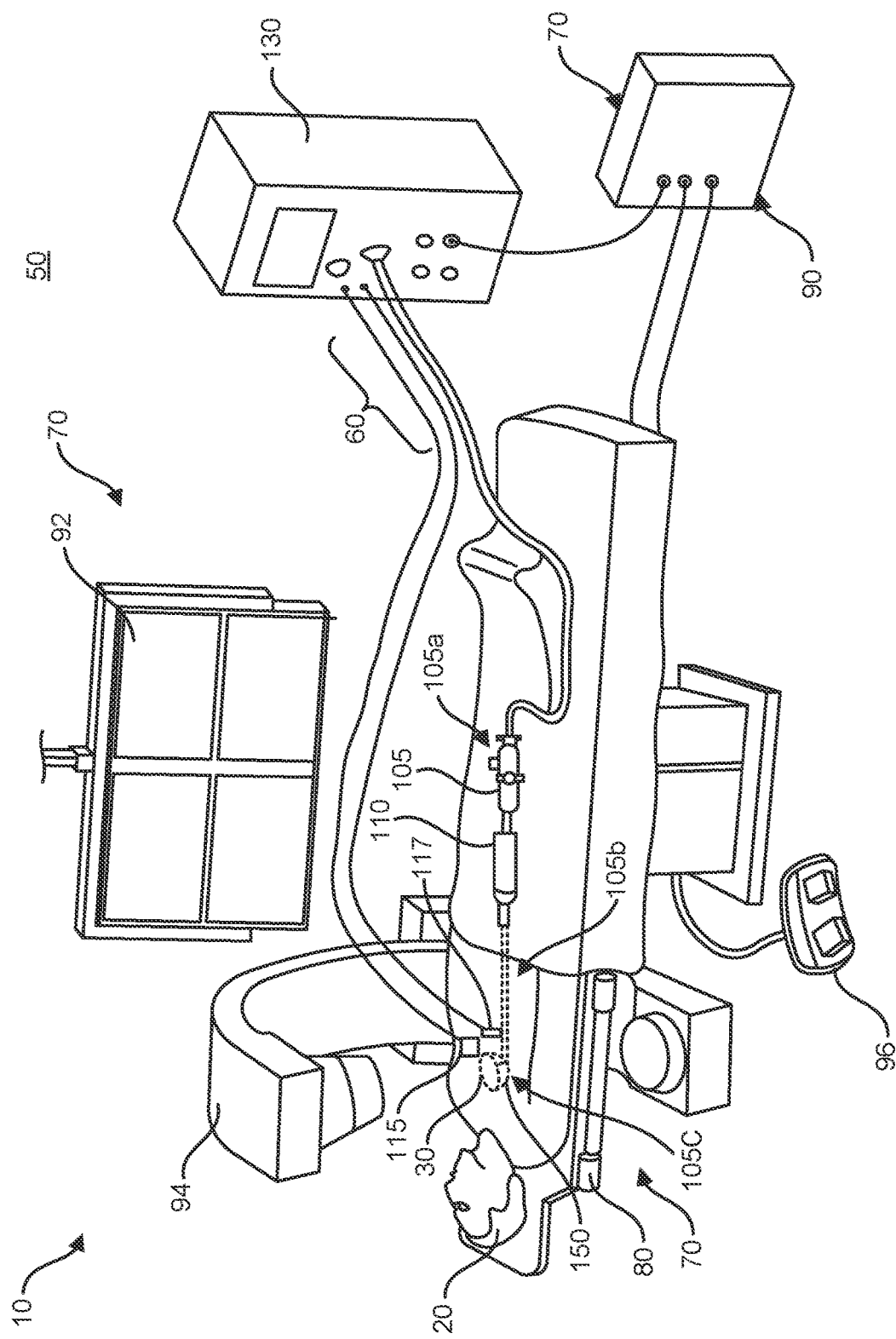
FIG. 1 is a diagram illustrating an exemplary clinical setting for treating a patient and for treating a heart of the patient, using an electrophysiology system, in accordance with embodiments of the subject matter of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

FIG. 1 is a diagram illustrating an exemplary clinical setting 10 for treating a patient 20, and for treating a heart 30 of the patient 20, using an electrophysiology system 50, in accordance with embodiments of the subject matter of the disclosure. The electrophysiology system 50 includes an electroporation system 60 and an electro-anatomical mapping (EAM) system 70, which includes a localization field generator 80, a mapping and navigation controller 90, and a display 92. Also, the clinical setting 10 includes additional equipment such as imaging equipment 94 (represented by the C-arm) and various controller elements, such as a foot controller 96, configured to allow an operator to control various aspects of the electrophysiology system 50. As will be appreciated by the skilled artisan, the clinical setting 10 may have other components and arrangements of components that are not shown in FIG. 1.

The electroporation system 60 includes an electroporation catheter 105, an introducer sheath 110, a surface patch electrode 115, and an electroporation generator 130. Also, in embodiments, the electroporation system 60 includes an accelerometer 117, where the accelerometer 117 can be a separate sensor or part of the surface electrode patch 115. Additionally, the electroporation system 60 includes various connecting elements (e.g., cables, umbilicals, and the like) that operate to functionally connect the components of the electroporation system 60 to one another and to the components of the EAM system 70. This arrangement of connecting elements is not of critical importance to the present disclosure, and one skilled in the art will recognize that the various components described herein may be interconnected in a variety of ways.

In embodiments, the electroporation system 60 is configured to deliver electric field energy to targeted tissue in the patient's heart 30 to create tissue apoptosis, rendering the tissue incapable of conducting electrical signals. The electroporation generator 130 is configured to control functional aspects of the electroporation system 60. In embodiments, the electroporation generator 130 is operable as a pulse generator for generating and supplying pulse sequences to the electroporation catheter 105 and the surface patch electrode 115, as described in greater detail herein. In embodiments, the electroporation generator 130 is operable to receive sensed signals from the accelerometer 117 and based on the received sensed signals act as a pulse generator for generating and supplying pulse sequences to the electroporation catheter 105 and the surface patch electrode 115, as described in greater detail herein.

In embodiments, the electroporation generator 130 includes one or more controllers, microprocessors, and/or computers that execute code out of memory to control and/or perform the functional aspects of the electroporation catheter system 60. In embodiments, the memory may be part of the one or more controllers, microprocessors, and/or computers, and/or part of memory capacity accessible through a network, such as the world wide web.

In embodiments, the introducer sheath 110 is operable to provide a delivery conduit through which the electroporation catheter 105 may be deployed to the specific target sites within the patient's heart 30. It will be appreciated, however, that the introducer sheath 110 is illustrated and described herein to provide context to the overall electrophysiology system 50, but it is not critical to the novel aspects of the various embodiments described herein.

The EAM system 70 is operable to track the location of the various functional components of the electroporation system 60, and to generate high-fidelity three-dimensional anatomical and electro-anatomical maps of the cardiac chambers of interest. In embodiments, the EAM system 70 may be the RHYTHMIA™ HDx mapping system marketed by Boston Scientific Corporation. Also, in embodiments, the mapping and navigation controller 90 of the EAM system 70 includes one or more controllers, microprocessors, and/or computers that execute code out of memory to control and/or perform functional aspects of the EAM system 70, where the memory, in embodiments, may be part of the one or more controllers, microprocessors, and/or computers, and/or part of memory capacity accessible through a network, such as the world wide web.

As will be appreciated by the skilled artisan, the depiction of the electrophysiology system 50 shown in FIG. 1 is intended to provide a general overview of the various components of the system 50 and is not in any way intended to imply that the disclosure is limited to any set of components or arrangement of the components. For example, the skilled artisan will readily recognize that additional hardware components, e.g., breakout boxes, workstations, and the like, may and likely will be included in the electrophysiology system 50.

The EAM system 70 generates a localization field, via the field generator 80, to define a localization volume about the heart 30, and one or more location sensors or sensing elements on the tracked device(s), e.g., the electroporation catheter 105, generate an output that may be processed by the mapping and navigation controller 90 to track the location of the sensor, and consequently, the corresponding device, within the localization volume. In the illustrated embodiment, the device tracking is accomplished using magnetic tracking techniques, whereby the field generator 80 is a magnetic field generator that generates a magnetic field defining the localization volume, and the location sensors on the tracked devices are magnetic field sensors.

In other embodiments, impedance tracking methodologies may be employed to track the locations of the various devices. In such embodiments, the localization field is an electric field generated, for example, by an external field generator arrangement, e.g., surface electrodes, by intra-body or intra-cardiac devices, e.g., an intracardiac catheter, or both. In these embodiments, the location sensing elements may constitute electrodes on the tracked devices that generate outputs received and processed by the mapping and navigation controller 90 to track the location of the various location sensing electrodes within the localization volume.

In embodiments, the EAM system 70 is equipped for both magnetic and impedance tracking capabilities. In such embodiments, impedance tracking accuracy can, in some instances, be enhanced by first creating a map of the electric field induced by the electric field generator within the cardiac chamber of interest using a probe equipped with a magnetic location sensor, as is possible using the aforementioned RHYTHMIA HDx™ mapping system. One exemplary probe is the INTELLAMAP ORION™ mapping catheter marketed by Boston Scientific Corporation.

Regardless of the tracking methodology employed, the EAM system 70 utilizes the location information for the various tracked devices, along with cardiac electrical activity acquired by, for example, the electroporation catheter 105 or another catheter or probe equipped with sensing electrodes, to generate, and display via the display 92, detailed three-dimensional geometric anatomical maps or representations of the cardiac chambers as well as electro-anatomical maps in which cardiac electrical activity of interest is superimposed on the geometric anatomical maps. Furthermore, the EAM system 70 may generate a graphical representation of the various tracked devices within the geometric anatomical map and/or the electro-anatomical map.

While the EAM system 70 is shown in combination with the electroporation system 60 to provide a comprehensive depiction of an exemplary clinical setting 10, the EAM system 70 is not critical to the operation and functionality of the electroporation system 60. That is, in embodiments, the electroporation system 60 can be employed independently of the EAM system 70 or any comparable electro-anatomical mapping system.

In the illustrated embodiment, the electroporation catheter 105 includes a handle 105a, a shaft 105b, and an electroporation electrode arrangement 150, which is described further hereinafter. The handle 105a is configured to be operated by a user to position the electroporation electrode arrangement 150 at the desired anatomical location. The shaft 105b has a distal end 105c and generally defines a longitudinal axis of the electroporation catheter 105. As shown, the electroporation electrode arrangement 150 is located at or proximate the distal end 105c of the shaft 105b. In embodiments, the electroporation electrode arrangement 150 is electrically coupled to the electroporation generator 130, to receive electrical pulse sequences or pulse trains, thereby selectively generating electrical fields for ablating the target tissue by irreversible electroporation.

In embodiments, the surface patch electrode 115 includes a conductive electrode that can be attached to the body of the patient 20, such as to the thorax of the patient. The surface patch electrode 115, including the conductive electrode, is electrically coupled to the electroporation generator 130 to act as a return path or sink for electrical energy in the system and to receive electrical pulse sequences or pulse trains from the electroporation generator 130, thereby acting as a source for electrical energy and selectively generating electrical fields for ablating the target tissue by irreversible electroporation. In embodiments, the surface patch electrode 115 acts as a return or sink for electrical energy received by the electroporation catheter 105 and the electroporation electrode arrangement 150. In embodiments, the surface patch electrode 115 acts as a source for electrical energy and the electroporation catheter 105 including the electroporation electrode arrangement 150 acts as the return or sink for the sourced electrical energy.

The electroporation system 60 is operable to generate an IRE pulse sequence that includes a preconditioning (pre-treatment) pulse sequence and an electroporation pulse sequence. The IRE pulse sequence is configured to ablate targeted tissue. In embodiments, the preconditioning pulse sequence is a series of electrical pulses that ramp up in magnitude to tetanize skeletal muscle tissue and to provide electrolysis near targeted tissue. In embodiments, the electroporation pulse sequence is a series of electroporation pulses configured to cause irreversible damage to the targeted tissue.

In embodiments, the electroporation system 60 includes the accelerometer 117 that may be attached to the body of the patient 20, such as to the thorax of the patient, and electrically coupled to the electroporation generator 130. The accelerometer 117 is configured to sense contraction of the skeletal muscle system of the patient to detect tetany. The signals from the accelerometer 117 are received by the electroporation generator 130, which processes the signals to determine whether the skeletal muscle system of the patient is contracting and whether tetany has been achieved. In embodiments, the electroporation generator 130 is configured to provide the electroporation pulse sequence only after tetany has been achieved in the patient.

In embodiments, the electroporation system 60 acts as a closed system with the surface accelerometer 117 monitoring chest vibrations and the electroporation generator 130 modulating pulses until tetany is achieved and then the electroporation generator 130 delivers the electroporation pulses. Also, in embodiments, the local impedance of the target tissue and tissue surrounding the target tissue can be measured during this time to calculate pre-ablation and post-ablation values for evaluation of the lesion efficacy.

Figure 2A:
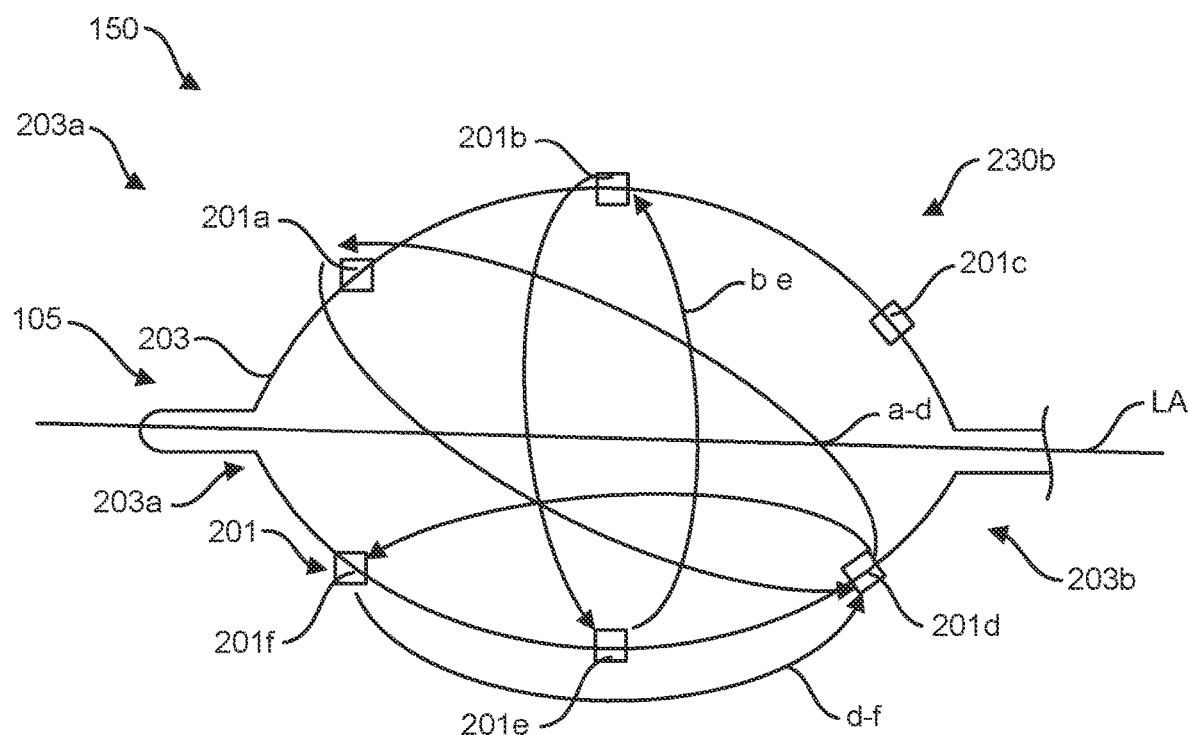
FIG. 2A is a diagram illustrating a distal end of a shaft included in a catheter and interactions between electrode pairs, in accordance with embodiments of the subject matter of the disclosure.
Figure 2B:
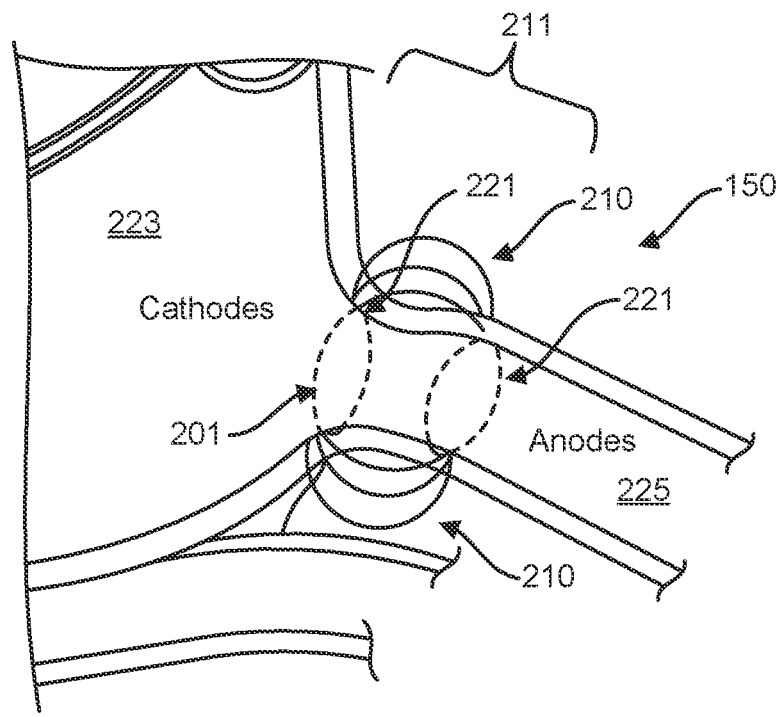
FIG. 2B is a diagram illustrating axial electric fields generated by interactions between electrode pairs, in accordance with embodiments of the subject matter of the disclosure.
Figure 2C:
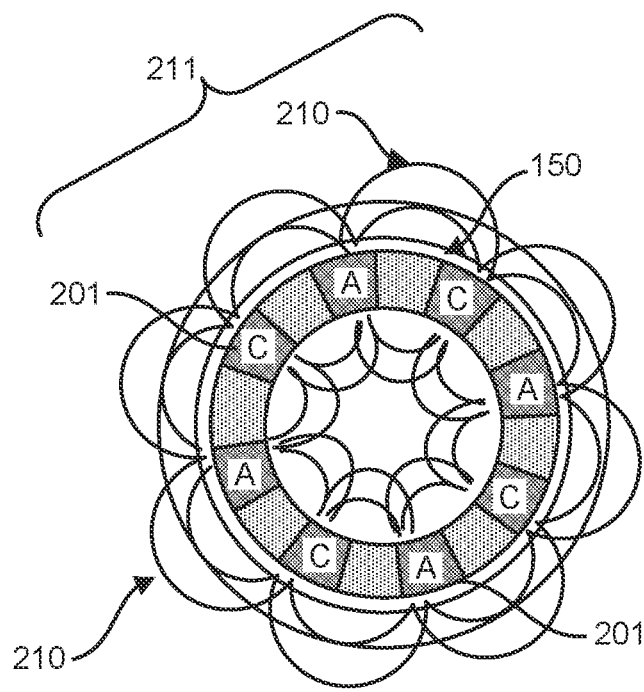
FIG. 2C is a diagram illustrating circumferential electric fields generated by interactions between electrode pairs in the catheter, in accordance with embodiments of the subject matter of the disclosure.

FIGS. 2A-2C show features of the electroporation catheter 105 that includes the electroporation electrode arrangement 150 according to exemplary embodiments. In the illustrated embodiment in FIG. 2A, the electroporation electrode arrangement 150 includes a plurality of electrodes 201a, 201b, 201c, 201d, 201e, and 201f arranged in a three-dimensional electrode array, such that respective ones of the electrodes 201a, 201b, 201c, 201d, 201e, and 201f are spaced from one another axially (i.e., in the direction of the longitudinal axis LA), circumferentially about the longitudinal axis LA and/or radially relative to the longitudinal axis LA. In some embodiments, the electrodes 201a, 201b, 201c, 201d, 201e, and 201f are each individually, selectively addressable via the electroporation generator 130 (FIG. 1) to define a plurality of anode-cathode electrode pairs, each capable of receiving an electrical pulse sequence from the electroporation generator 130 and, consequently, creating an electric field capable of selectively targeting tissue via electroporation, including ablating target tissue via IRE. FIG. 2A schematically illustrates interactions (e.g., current flows forming electric fields) between electrode pairs formed between electrodes 201 (e.g., 201a, 201b, 201c, 201d, 201e, and 201f) included in the electroporation catheter 105. In this figure, interactions are shown as paired arrows (e.g., a-d, b-e, and d-f) indicating current flows between electrodes 201. And electrode pairs (e.g., 201a and 201d, 201b and 201e, and 201d and 201f) are shown with their respective current flows (e.g., a-d, b-e, and d-f) labeled.

FIG. 2B is a diagram illustrating electric fields 210 generated by interactions between electrode pairs in the electroporation catheter 105. In this figure, axially oriented electric fields 210 are shown positioned at an ostium 221 between the left atrium 223 and the left inferior pulmonary vein 225. In embodiments, the axially oriented electric fields 210 are produced by delivering electrical pulses to axially spaced anodes and cathodes.

FIG. 2C is also a diagram illustrating electric fields 210 generated by interactions between electrode pairs in the electroporation catheter 105. But here, the electric fields 210 are circumferentially oriented. In embodiments, the circumferentially oriented electric fields 210 are produced by delivering electrical pulses to circumferentially spaced anodes ("A") and cathodes ("C").

FIGS. 2A-2C show that multiple electric fields 210 may be generated simultaneously and/or sequentially and in axial and circumferential orientations. For example, in embodiments, axially and circumferentially oriented electric fields 210 can be generated non-simultaneously in a pre-defined sequence by selectively controlling the timing of the delivery of the electric pulses to the respective electrodes 201. In addition, it is understood that intermittently generated electric fields 210 caused by staggered interactions between sets of electrode pairs and electric field orientations other than axial and circumferential are not beyond the scope of this disclosure.

As may be seen in FIG. 2A, the electroporation electrode arrangement 150 may include a plurality of individually addressable electrodes 201 (e.g., anodes or cathodes) arranged to selectively define a plurality of electrode pairs (e.g., anode-cathode pairs). Each anode-cathode pair may be configured to generate an electric field when a pulse sequence is delivered thereto. The plurality of anode-cathode pairs may include at least two of a first anode-cathode pair, a second anode-cathode pair, and a third anode-cathode pair. The first anode-cathode pair may be arranged to generate a first electric field oriented generally circumferentially relative to the longitudinal axis when a first pulse sequence is delivered thereto. The second anode-cathode pair may be arranged to generate a second electric field oriented generally in a same direction as the longitudinal axis when a second pulse sequence is delivered thereto. The third anode-cathode pair may be arranged to generate a third electric field oriented generally transverse to the longitudinal axis when a third pulse sequence is delivered thereto. In embodiments, any combination of the first, second, and third pulse sequences may be delivered simultaneously or intermittently and may take a variety of forms.

In embodiments, the electroporation electrode arrangement 150 may be configured to structurally arrange the electrodes 201a, 201b, 201c, 201d, 201e, and 201f into a distally-located first region and a more proximally-located second region. As such, electrode pairs may be formed across various electrodes 201 in the electroporation electrode arrangement 150 between first and second regions. For example, the electrodes 201d and 201f may be configured to form an electrode pair. Similarly, the electrodes 201a and 201d or electrodes 201b and 201e or the combination thereof may be selected to form respective electrode pairs. Thus, the electrode pairs may comprise axially spaced electrodes, transversely spaced electrodes, or circumferentially spaced electrodes. Additionally, in embodiments, a given electrode (e.g., 201d) may serve as a common electrode in at least two electrode pairs to generate electric fields 210.

FIG. 2B shows a diagram of exemplary electric fields 210 that may be generated by the electroporation electrode arrangement 150. The electroporation electrode arrangement 150 may be configured to generate a multidirectional electric field 210 when at least one pulse sequence is delivered thereto. The multidirectional electric field 210 may include at least two of the following directions relative to the longitudinal axis: generally axial, circumferential, and transverse. As used herein, transverse may mean at any non-parallel angle relative to the longitudinal axis. As described elsewhere herein, the electroporation electrode arrangement 150 may be configured to operatively couple to an electroporation generator that is configured to generate the at least one pulse sequence. The electroporation electrode arrangement 150 may be configured to receive the at least one pulse sequence from the electroporation generator. Thus, the electroporation electrode arrangement 150 and the electroporation generator may be in operative communication with each other. In this disclosure, such communication may be used to generate electric fields 210 that are at least substantially gapless.

Undesired gaps in electric fields 210 generated by the electroporation electrode arrangement 150 may be limited or at least substantially eliminated. Such gaps may potentially lead to lesion gaps and therefore require multiple repositions of a catheter, for example. Overlapping electric fields 210 may at least substantially limit the number of such gaps. In embodiments, at least some the electric fields 210 generated in the first pulse sequence set may overlap at least partially with each other. For example, adjacent electric fields 210 (e.g., axial, transverse, and/or circumferential) in a combined electric field 211 may intersect one another so that there are limited to no gaps in the combined electric field 211. Overlapping may occur at or near the periphery of adjacent electric fields 210 or may occur over a preponderance or majority of one or more adjacent electric fields 210. In this disclosure, adjacent means neighboring electrodes 201 or electrodes 201 otherwise near each other. The electroporation generator may be configured to generate pulse sequences used in generating overlapping electric fields.

The configuration of the electroporation electrode arrangement 150 in the various embodiments may take on any form, whether now known or later developed, suitable for a three-dimensional electrode structure. In exemplary embodiments, the electroporation electrode arrangement 150 may be in the form of a splined basket catheter, with respective electrodes 201a, 201b, 201c, 201d, 201e, and 201f positioned on a plurality of splines in any manner known in the art. In embodiments, the electroporation electrode arrangement 150 can be formed on an expandable balloon, e.g., with electrodes formed on flexible circuit branches or individual traces disposed on the balloon surface. In other embodiments, the electroporation electrode arrangement 150 may be in the form of an expandable mesh. In short, the particular structure used to form the electroporation electrode arrangement 150 is not critical to the embodiments of the present disclosure.

Figure 3:
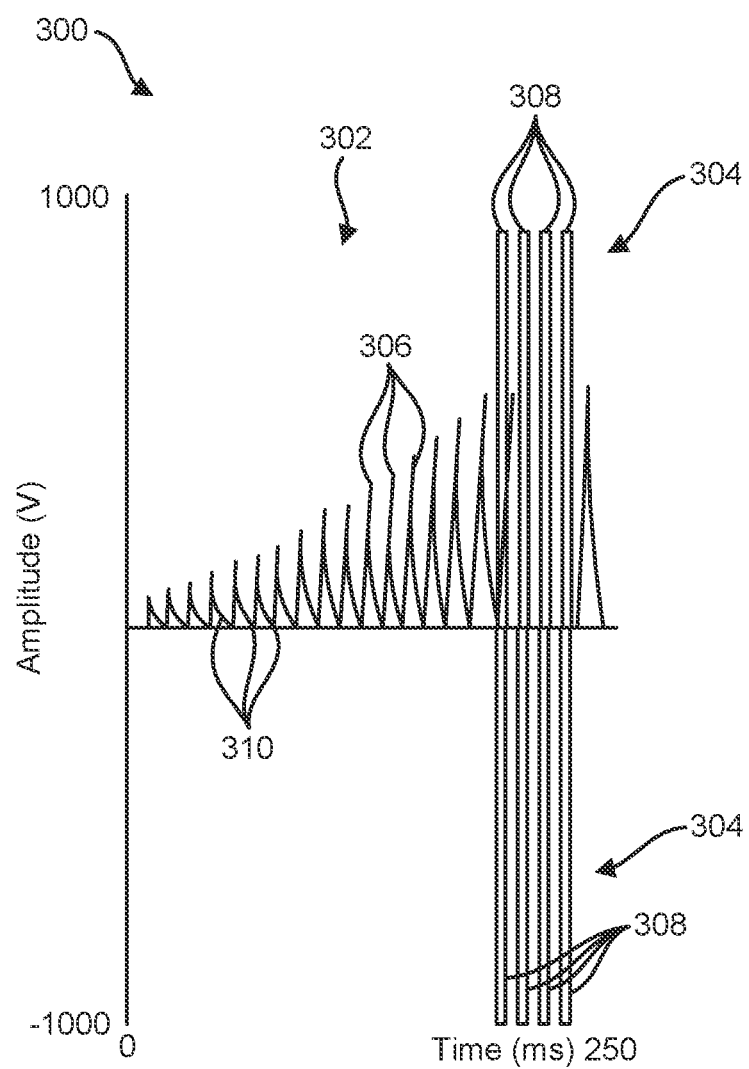
FIG. 3 is a diagram illustrating an IRE pulse sequence that includes a preconditioning pulse sequence and an electroporation pulse sequence, in accordance with embodiments of the subject matter of the disclosure.

FIG. 3 is a diagram illustrating an ablation energy application sequence 300, also referred to herein as an IRE pulse sequence 300, that includes a preconditioning pulse sequence 302 and an electroporation pulse sequence 304, in accordance with exemplary embodiments. The preconditioning pulse sequence 302 is a series of pulses 306 that ramp up in magnitude from a lower voltage to a higher voltage. The electroporation pulse sequence 304 is a series of high energy electroporation pulses 308 having large positive and/or negative voltage values.

The electroporation system 60 is configured to deliver the preconditioning pulse sequence 302, which delivers the series or sequence of pulses 306 for achieving tetany and for generating electrolysis. In FIG. 3, only three pulses 306 of the preconditioning pulse sequence 302 are pointed to for clarity in the figure, however, in embodiments, the sequence of pulses 306 includes all the pulses in the preconditioning pulse sequence 302. The electroporation system 60 is further configured to deliver the electroporation pulse sequence 304, i.e., electroporation ablation energy, in the series of electroporation pulses 308 to ablate the targeted tissue. In embodiments, all pulses in the IRE pulse sequence 300 are delivered within the refractory period of the heart, such as within 250-330 milliseconds.

The sequence of pulses 306 is a series of monophasic pulses that ramp up in magnitude from a lower voltage to a higher voltage over time. The ramping of voltage causes relatively slower recruitment of skeletal muscles culminating in the tetanic skeletal muscle contraction preceding the higher voltage electroporation pulses 308 in the electroporation pulse sequence 304. Each of the pulses 306, or at least some of the pulses 306, also have features that promote electrolysis, such as including a monophasic exponentially decaying waveform 310 (or drooping waveform) on the back side of the pulse 306. In FIG. 3, only three of the exponentially decaying waveforms 310 in the preconditioning pulse sequence 302 are pointed to for clarity in the figure, however, in embodiments, all the pulses in the preconditioning pulse sequence 302 include exponentially decaying waveforms 310. In embodiments, the pulses 306 may not be completely monophasic, but include at least some asymmetrical phases that are charge balanced with both positive and negative components. In some embodiments, the duration of the pulses 306 is between 1 millisecond (ms) and 60 ms and, in some embodiments, the waveform tilt/droop/exponential decay is in the range of 20 to 80% of the leading edge.

The pulses 306 can have a number of different characteristics. In embodiments, the pulses 306 in the preconditioning pulse sequence 302 are provided at a selected frequency, such as 1 kilohertz. In some embodiments, this frequency is in the range of 200-1000 Hz. In embodiments, the pulses 306 are ramped up in voltage from 0 volts to between 5 and 100 volts and, in some embodiments, the amplitude reaches between 100 and 1000 volts. Also, in embodiments, ramping rates can be incrementing 1% to 30% of the preceding pulse. In some embodiments, the preconditioning pulse sequence 302 is applied in a 100-250 millisecond sequence duration.

The preconditioning pulse sequence 302 preconditions the body for electroporation in at least two ways. First, the preconditioning pulse sequence 302 acts as a series of tetanizing skeletal muscle pulses 306 that cause tetany, i.e., contraction of the skeletal muscles of the patient's body, prior to receiving the higher voltage electroporation pulse sequence 304. Ramping the pulses 306 up in magnitude from a lower voltage to a higher voltage over time causes or contributes to bringing about tetany. This SMS prepares the patient for the higher voltage electroporation pulses 308 in the electroporation pulse sequence 304, which otherwise may shock the patient or be a painful experience for the patient. Second, the preconditioning pulse sequence 302 acts as a series of electrolysis inducing pulses 306 that cause electrolysis near the target tissue. This results in creating a cytotoxic environment near the target tissue, such that smaller electroporation pulses can be used to permeabilize the target tissue and cause cell death, creating larger lesions with smaller electroporation pulses.

This synergistic electrolysis is caused by applying relatively long, low voltage pulses, such as the preconditioning pulse sequence 302, to the target area. In particular, the exponentially decaying waveforms 310 (or drooping waveforms) on the back side of the pulses 306 of the preconditioning pulse sequence 302 bring about electrolysis near the electrodes. In further explanation, synergistic electrolysis occurs when new chemical species are generated at the interface of the electrodes as a result of electron transfer between the electrodes and the ions in solution. The new chemical species diffuse away from the electrodes, into tissue, in a process driven by electrochemical potentials. In physiological solutions, electrolytic reactions yield changes in pH, resulting in an acidic region near the anode and a basic region near the cathode. The cytotoxic environment developing due to local changes in pH, and the presence of some of the new chemical species formed during electrolysis of the solution, along with permeabilization of electroporation cause cell death.

In exemplary embodiments, the preconditioning pulse sequence 302 is delivered as a series of unipolar electrical pulses 306. The surface patch electrode 115, attached to the thorax of the patient 20, receives the electrical pulses from the electroporation generator 130 and sources the electrical energy, where the surface patch electrode 115 acts as a source electrode for the electrical pulses. One or more electrodes on the electroporation catheter 105 sink the electrical energy that is sourced by the surface patch electrode 115, where the one or more electrodes on the electroporation catheter 105 act as a sink for the electrical pulses. This causes the skeletal muscles of the patient to contract, reaching tetany, and generates the synergistic electrolysis near the targeted tissue, where electrodes of the electroporation catheter 105 are situated near the targeted tissue.

In other embodiments, one or more electrodes on the electroporation catheter 105 receives the pulses 306 from the electroporation generator 130 and sources the electrical energy, such that the one or more electrodes on the electroporation catheter 105 act as a source electrode for the electrical pulses 306. The surface patch electrode 115, attached to the thorax of the patient 20, sinks the electrical energy that is sourced by the one or more electrodes on the electroporation catheter 105, such that the surface patch electrode 115 acts as a sink for the electrical pulses.

After delivering at least some of the preconditioning pulse sequence 302, the electroporation system 60 is configured to deliver the electroporation pulse sequence 304, i.e., electroporation ablation energy, to ablate the targeted tissue. The electroporation pulse sequence 304 includes high energy electroporation pulses 308 of short duration. As illustrated, the electroporation pulses 308 of the electroporation pulse sequence 304 are biphasic, including, for example, both positive pulses and negative pulses. In embodiments, the electroporation pulses 308 may be positive 1000 volts and negative 1000 volts. In other embodiments, the electroporation pulses 308 can be monophasic, including, for example, all positive pulses or all negative pulses.

With at least some of the pulses 206 of the preconditioning pulse sequence 302 applied prior to applying the electroporation pulses 308, electrolysis near or at the targeted tissue makes it possible to use electroporation pulses 308 that are lower in amplitude, such as from 250 volts/centimeter (V/cm) to 1000 V/cm, than what is normally or otherwise necessary when using electroporation pulses alone (500 V/cm to 2,500 V/cm).

As illustrated, the electroporation pulses 308 of the electroporation pulse sequence 304 are delivered within the series of pulses 306 of the preconditioning pulse sequence 302. In other embodiments, the electroporation generator 130 can be configured to deliver the electroporation pulses 308 of the electroporation pulse sequence 304 after all the pulses 306 of the preconditioning pulse sequence 302 have been delivered.

The electroporation pulses 308 of the electroporation pulse sequence 304 can be either unipolar pulses or bipolar pulses. In embodiments, pairs of electrodes (or electrode sets) on the electroporation catheter 105 are selected to deliver bipolar pulses between the selected pairs of electrodes. Each electrode of the pairs of electrodes can act as a source electrode and each electrode of the pairs of electrodes can act as a sink, to deliver the electrical ablation energy to the targeted tissue.

In other embodiments, to provide unipolar pulses, one or more electrodes on the electroporation catheter 105 receives the electroporation pulses 308 of the electroporation pulse sequence 304 from the electroporation generator 130 and sources the electrical energy, such that the one or more electrodes on the electroporation catheter 105 act as a source electrode for the electrical pulses. The surface patch electrode 115, attached to the thorax of the patient 20, sinks the electrical energy that is sourced by the one or more electrodes on the electroporation catheter 105, such that the surface patch electrode 115 acts as a sink for the electrical pulses.

In embodiments, the electroporation system 60 includes the accelerometer 117 that is configured to sense contraction of the skeletal muscles of the patient, such as contraction of the patient's chest muscles, to detect tetany. The signals from the accelerometer 117 are received by the electroporation generator 130, which processes the signals to determine whether the skeletal muscle system of the patient is contracting and whether tetany has been achieved. In embodiments, the electroporation generator 130 is configured to provide the electroporation pulse sequence 304 only after tetany has been achieved in the patient. The electroporation generator 130 may provide the electroporation pulse sequence 304 during the preconditioning pulse sequence 302 or after the preconditioning pulse sequence 302.

Thus, the electroporation system 60 acts as a closed system with the surface accelerometer 117 monitoring chest vibrations and the electroporation generator 130 modulating pulses 306 until tetany is achieved and then delivering the electroporation pulses 308. Also, in embodiments, the local impedance of the target tissue and tissue surrounding the target tissue can be measured during this time to calculate pre-ablation and post-ablation values for evaluation of the lesion efficacy.

By applying at least some of the pulses 306 in the preconditioning pulse sequence 302 prior to delivering the electroporation pulses 308 of the electroporation pulse sequence 304, tetany or a contracting of the skeletal muscles of the patient can be achieved and, via electrolysis, a cytotoxic environment can be established near or adjacent the targeted tissue prior to delivering the electroporation pulses 308 of the electroporation pulse sequence 304. This results in being able to use lower energy electroporation pulses 308 and/or fewer electroporation pulses 308 to create the same size lesion as may be created using much more energetic or many more electroporation pulses 308 without the preconditioning pulse sequence 302.

Figure 4:
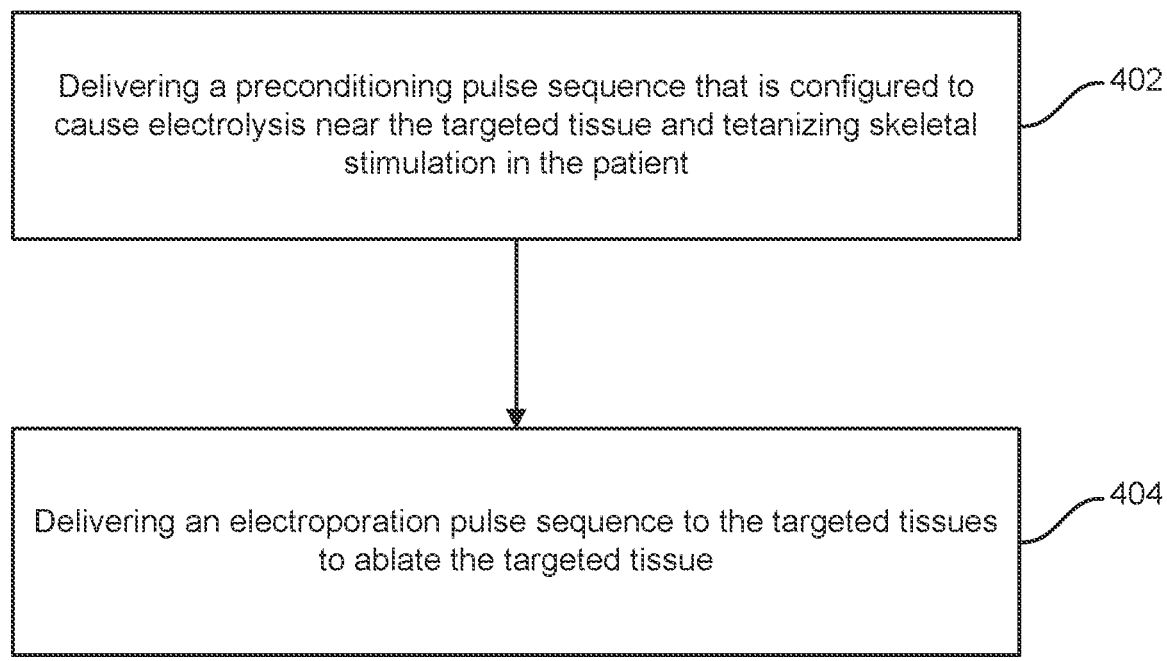
FIG. 4 is a flow chart diagram illustrating a method of ablating targeted tissue in a patient by irreversible electroporation, in accordance with embodiments of the subject matter of the disclosure.

FIG. 4 is a flow chart diagram illustrating a method of ablating targeted tissue in a patient by irreversible electroporation, in accordance with embodiments of the subject matter of the disclosure. Such a method and other related methods of ablating targeted tissue in a patient by irreversible electroporation are disclosed herein.

The method includes delivering an IRE (irreversible electroporation) pulse sequence that includes delivering a preconditioning pulse sequence at 402 and delivering an electroporation pulse sequence at 404. In embodiments, the electroporation pulse sequence is delivered during or within the preconditioning pulse sequence. In other embodiments, the electroporation pulse sequence is delivered after the preconditioning pulse sequence has stopped. In exemplary embodiments, the IRE pulse sequence, including the preconditioning pulse sequence and the electroporation pulse sequence, is delivered to the patient in one or more of a refractory time of the heart of the patient, less than 330 milliseconds, and in a 100-250 millisecond window.

Delivering the preconditioning pulse sequence at 402 includes delivering the preconditioning pulse sequence between a surface patch electrode and one or more catheter electrodes on a catheter to cause electrolysis near the targeted tissue and tetanizing skeletal muscle stimulation in the patient. In embodiments, the preconditioning pulse sequence includes unipolar electrical pulses that are sourced from the surface patch electrode and sunk through the one or more catheter electrodes. In other embodiments, the preconditioning pulse sequence includes unipolar electrical pulses that are sourced from the one or more catheter electrodes and sunk through the surface patch electrode. Also, in embodiments, the preconditioning pulse sequence includes preconditioning pulses that are monophasic.

The preconditioning pulse sequence includes preconditioning pulses delivered at a selected frequency and ramped up in voltage from a lower voltage to a higher voltage over time. In embodiments, the preconditioning pulse sequence includes preconditioning pulses delivered at about 1 kilohertz. Also, in embodiments, the preconditioning pulse sequence includes preconditioning pulses ramped up in voltage from 0 volts to between 5 and 100 volts. Ramping up the voltage of the pulse from a lower voltage to a higher voltage over time, contributes to causing tetanizing skeletal muscle contraction in the patient. Also, the preconditioning pulse sequence includes preconditioning pulses that include an exponentially decaying backside waveform that causes or contributes to electrolysis near the targeted tissue.

Delivering an electroporation pulse sequence at 404 includes delivering the electroporation pulse sequence to catheter electrodes on the catheter to cause irreversible electroporation ablation of the targeted tissue. In embodiments, the electroporation pulse sequence includes bipolar electrical pulses delivered to one or more catheter electrode pairs of the catheter electrodes. In other embodiments, the electroporation pulse sequence includes unipolar electrical pulses delivered between the surface patch electrode and one or more catheter electrodes on the catheter.

In embodiments, the method further includes monitoring the accelerometer 117 on the patient, which is configured to sense contraction of the skeletal muscles of the patient, such as contraction of the patient's chest muscles, to detect tetany. In a closed loop system, the signals from the accelerometer 117 are received by the electroporation generator 130, which processes the signals to determine whether the skeletal muscle system of the patient is contracting and whether tetany has been achieved. In embodiments, the electroporation generator 130 is configured to provide the electroporation pulse sequence only after tetany has been achieved in the patient, which may be during the preconditioning pulse sequence or after the preconditioning pulse sequence.

Also, in embodiments, the method includes monitoring the local impedance of the target tissue and tissue surrounding the target tissue to calculate pre-ablation and post-ablation values for evaluation of the lesion efficacy.

Various modifications and additions may be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

I claim:

1. An electroporation ablation system for treating targeted tissue in a patient, the electroporation ablation system comprising:
   an ablation catheter including:
      a handle;
      a shaft having a distal end; and
      catheter electrodes situated at the distal end of the shaft and spatially arranged to generate electric fields in the targeted tissue in response to electrical pulses; and
   an electroporation generator operatively coupled to the catheter electrodes and configured to deliver the electrical pulses in an irreversible electroporation pulse sequence that includes a preconditioning pulse sequence and an electroporation pulse sequence to one or more of the catheter electrodes,
   wherein the preconditioning pulse sequence includes preconditioning electrical pulses configured to cause electrolysis near the targeted tissue and tetanizing skeletal muscle stimulation in the patient.

2. The electroporation ablation system of claim 1, comprising a surface patch electrode attached to the patient and configured to generate electric fields in the patient in response to the electrical pulses.

3. The electroporation ablation system of claim 1, wherein the preconditioning pulse sequence includes unipolar electrical pulses that are sourced from the surface patch electrode and sunk through the one or more of the catheter electrodes.

4. The electroporation ablation system of claim 1, wherein the preconditioning pulse sequence includes unipolar electrical pulses that are sourced from the one or more of the catheter electrodes and sunk through the surface patch electrode.

5. The electroporation ablation system of claim 1, wherein the preconditioning pulse sequence includes bipolar electrical pulses that are sourced from at least one of the one or more catheter electrodes and sunk through at least another one of the one or more catheter electrodes.

6. The electroporation ablation system of claim 1, wherein the preconditioning pulse sequence includes preconditioning pulses delivered at a selected frequency.

7. The electroporation ablation system of claim 1, wherein the preconditioning pulse sequence includes preconditioning pulses ramped up in voltage from a lower voltage to a higher voltage over time.

8. The electroporation ablation system of claim 1, wherein the preconditioning pulse sequence includes preconditioning pulses that include an exponentially decaying backside waveform configured to cause electrolysis near the targeted tissue.

9. The electroporation ablation system of claim 1, wherein the preconditioning pulse sequence includes preconditioning pulses that are monophasic.

10. The electroporation ablation system of claim 1, wherein the irreversible electroporation pulse sequence, including the preconditioning pulse sequence and the electroporation pulse sequence, is delivered to the patient in one or more of a refractory time of a heart of the patient, for less than 330 milliseconds, and in a 100-250 millisecond window.

11. The electroporation ablation system of claim 1, wherein the electroporation pulse sequence is delivered within the preconditioning pulse sequence.

12. The electroporation ablation system of claim 1, wherein the electroporation pulse sequence includes bipolar electrical pulses delivered to one or more catheter electrode pairs of the one or more of the catheter electrodes.

13. The electroporation ablation system of claim 1, comprising an accelerometer configured to monitor skeletal muscle stimulation of the patient and wherein the electroporation ablation system is a closed loop system such that the electroporation generator is configured to deliver the preconditioning pulse sequence, detect tetany in the patient, and then deliver the electroporation pulse sequence, and wherein local impedance is measured to calculate pre-ablation and post-ablation values to evaluate lesion efficacy.

14. An electroporation ablation system for treating targeted tissue in a patient, the electroporation ablation system comprising:
    an ablation catheter including:
        a handle;
        a shaft having a distal end; and
        catheter electrodes situated at the distal end of the shaft and spatially arranged to generate electric fields in the targeted tissue in response to receiving electrical pulses; and
    an electroporation generator operatively coupled to multiple electrodes including one or more of a surface patch electrode and one or more of the catheter electrodes and configured to deliver the electrical pulses in an irreversible electroporation pulse sequence that includes a preconditioning pulse sequence and an electroporation pulse sequence to the multiple electrodes, wherein the electroporation generator is configured to deliver the electroporation pulse sequence during the preconditioning pulse sequence;
    wherein the preconditioning pulse sequence includes preconditioning electrical pulses configured to cause electrolysis near the targeted tissue and tetanizing skeletal muscle stimulation in the patient.

15. The electroporation ablation system of claim 14, wherein the electroporation pulse sequence includes bipolar electrical pulses delivered to selected pairs of the one or more catheter electrodes.

16. A method of ablating targeted tissue in a patient by irreversible electroporation, the method comprising:
    delivering an irreversible electroporation pulse sequence comprising:
        delivering a preconditioning pulse sequence between multiple electrodes including one or more of a surface patch electrode and one or more catheter electrodes on a catheter to cause electrolysis near the targeted tissue and tetanizing skeletal muscle stimulation in the patient; and
        delivering an electroporation pulse sequence to the multiple electrodes to cause irreversible electroporation ablation of the targeted tissue.

17. The method of claim 16, wherein delivering a preconditioning pulse sequence includes delivering electrical pulses that ramp up in voltage from a lower voltage to a higher voltage over time and wherein one or more of the electrical pulses include an exponentially decaying backside waveform.

18. The method of claim 16, wherein the electroporation pulse sequence is delivered during the preconditioning pulse sequence.

19. The method of claim 16, comprising monitoring an accelerometer on the patient and in a closed loop system, delivering the preconditioning pulse sequence to achieve the tetany in the patient, detecting tetany in the patient via the accelerometer, and delivering the electroporation pulse sequence after tetany has been achieved.

\* \* \* \* \*